United States Patent
Raghukumar et al.

(10) Patent No.: US 7,118,906 B2
(45) Date of Patent: *Oct. 10, 2006

(54) PROCESS FOR REMOVAL OF POLYCYCLIC AROMATIC HYDROCARBONS IN WASTEWATER AND OTHER CONTAMINATED SITES

(75) Inventors: Chandralata Raghukumar, Goa (IN); Mysore Srinivasa-Murthy Shailaja, Goa (IN); Shilpa Kamat, Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 353 days.

This patent is subject to a terminal disclaimer.

(21) Appl. No.: 10/124,579

(22) Filed: Apr. 18, 2002

(65) Prior Publication Data

US 2003/0003569 A1   Jan. 2, 2003

Related U.S. Application Data

(63) Continuation-in-part of application No. 09/456,559, filed on Dec. 8, 1999, now Pat. No. 6,395,534.

(30) Foreign Application Priority Data

Mar. 31, 1999   (IN) .............................. 494/DEL/99

(51) Int. Cl.
   *B09C 1/10*   (2006.01)
(52) U.S. Cl. .............................. 435/262.5; 435/254.1; 435/911
(58) Field of Classification Search ............. 435/262.5, 435/254.1, 911
   See application file for complete search history.

(56) References Cited

U.S. PATENT DOCUMENTS 5,091,089 A   2/1992   Shen et al. ................. 210/611
5,755,514 A   5/1998   Baar-Bartelt ................ 383/104

FOREIGN PATENT DOCUMENTS

DE   290 004   12/1989 ...................... 3/34
JP   6-47394   2/1994 ...................... 3/32

OTHER PUBLICATIONS

Tien, et al., Lignin Peroxidase of phanerochaete Chrysosporium; Methods in Enzymology, vol. 161, pp. 238-249.
Niku-Paavola, et al., Ligninolytic Encymes of the Ehite-Rot Fungus Phlebia Radiata, Biochem. J. 1988, vol. 254, pp. 877-883.
Gold, et al., Use of Polymeric Dyes in Lignin Biodegradation Assays, Methods in Enzymology, 1978, vol. 161, pp. 74-78.
Paszczynshi, et al., Manganese Peroxidase of Phanerochaete Chrysosporium: Purification, Methods in Enzymology, vol. 161, pp. 264-270.
Reddy, The Potential for While-Rot Fungi in the Treatment of Pollutants, Environmental Biotechnology, 1995, vol. 6, pp. 320-328.
Heinfling, et al., Biodegradation of AZO and Phthalocyanine Dyes by Trametes Versicolot and Bjerkandera Adusta; appl. Microbiol. Biotechnol. 1997, vol. 48, pp. 261-228.
Rattan, et al., J. Res (Punjab Agric. Univ.), (1983 (RECD 1984) 20(2), 228-229.
Purkayastha, et al., Proceedings of the Indian National Science Academy Part B Biological Sciences, (1994) vol. 60, No. 3, pp. 269-275.
Bumpus, et al., Biodegradation of Crystal Violet by the White Rot Fungus; Biology Department and the Biotechnology Center, Utah State University, Logan, Utah; Received Sep. 8, 1987/Accepted Jan. 30, 1988; vol. 54, No. 5, pp. 1143-1150.
Raghukumar, et al., Lignin-Modifying Enzymes of Flavodan flavus, a Basidiomycete Isolated from a Coastal Marine Environment; Department of Microbiology and NSF Center for Microbial Ecology; Received Nov. 6, 1998/Accepted Feb. 11, 1999; vol. 65, No. 5, pp. 2103-2111.

*Primary Examiner*—Irene Marx
(74) *Attorney, Agent, or Firm*—Smith, Gambrell & Russell, LLP

(57) ABSTRACT

The present invention particularly relates to a process of removal of polycyclic aromatic hydrocarbons phenanthrene and chrysene from wastewater and other contaminated sites by using a white-rot fungus *Flavodon flavus* (K 1) Ryv., which has been deposited at Agricultural Research Service Culture Collection (NRRL), 1815 North University Street, Peoria, Ill. 61604, USA bearing accession number NRRL 30302 on Mar. 10, 2000.

17 Claims, 6 Drawing Sheets

PROCESS FOR REMOVAL OF POLYCYCLIC AROMATIC HYDROCARBONS IN WASTEWATER AND OTHER CONTAMINATED SITES

This application is a continuation in part of Ser. No. 09/456,559 filled Dec. 8, 1999 now U.S. Pat. No. 6,395,534.

The present application is a continuation-in-part application of U.S. application Ser. No. 09/456,559 which has been accepted and wherein a novel strain "*Flavodon flavus*" has been identified and which has been deposited at Agricultural Research Service Culture Collection (NRRL), 1815 North University Street, Peoria, Ill. 61604, USA bearing accession number NRRL 30302 on Mar. 10, 2000 and has also been deposited at National Institute of Oceanography, Dona Paula, Goa 403 004, India bearing accession number NIOCC # 312.

FIELD OF THE INVENTION

The present invention relates to a process for removal of three-ringed and four-ringed polycyclic aromatic hydrocarbons from wastewater and other contaminated sites. The present invention particularly relates to a process of removal of polycyclic aromatic hydrocarbons phenanthrene and chrysene from wastewater and other contaminated sites by using a white-rot fungus *Flavodon flavus* (K 1) Ryv., having accession No. NRRL 30302. Further the present invention relates to at least 70% removal of polycyclic aromatic hydrocarbons especially phenanthrene and chrysene from wastewater and other contaminated sites within 7 days using live or heat-killed culture of *Flavodon flavus*.

BACKGROUND AND PRIOR ART OF THE INVENTION

Polycyclic aromatic hydrocarbons (PAHs), such as three-ringed phenanthrene, four-ringed chrysene, are commonly found as pollutants in soils, estuarine waters and sediments and other aquatic sites. Phenanthrene has been shown to be toxic to marine diatoms (Kusk, 1981), gastropods (Pipe and Moore, 1986), mussels, crustaceans and fish (Black et al., 1983). Inoculation of pure microbial culture to biodegrade recalcitrant organic compounds has had increased interest in the field of biological treatment of polluted waters or wastewater effluents. Several bacteria and cyanobacteria are known to metabolise phenanthrene. White-rot fungi are also known to metabolise phenanthrene besides several other PAHs. White-rot fungi are known to metabolise several xenobiotic compounds due to extracellular production of lignin-degrading enzymes. Due to the importance attached to prevention of environmental pollution, environmental agencies all over the world are imposing strict regulations for mitigation of pollution from industries and human activities. Therefore, search for newer and better sources of organisms for removal or bioremediation of toxic compounds remains a continuous process. *F. flavus* produces lignin-modifying enzymes such as manganese-dependent peroxidase E.C.1.11.1.7 (MNP), lignin peroxidase, E.C. 1.11.1.7 (LIP) and laccase, E.C. 1.10.3.2 when grown on sugarcane bagasse suspended in distilled water or in conventional media prepared with distilled water or half-strength sea water (Raghukumar et al. 1999a).

The fungus *Flavodon flavus* belonging to the class Basidiomycetes produces fertile basidiomata in medium containing alpha-cellulose and sometime in malt extract agar medium on a prolonged incubation. Most of the time this fungus is in non-sporulating form, off white to white in color, slimy looking mycelium and can be recognised by crystals deposited around fungal hyphae. Fruiting bodies from culture were identified as *Flavodon flavus* using the key in Ryvarden Johansen (Ryvarden, L. and I. Johansen, 1980. A preliminary polypore flora of East Africa, Fungiflora, Oslo, Norway). Most of the white-rot fungi do not grow in the presence of synthetic or natural seawater whereas, the strain *Flavodon flavus* isolated by the applicants from decaying seagrass, grows and produces lignin-degrading enzymes in the presence of half-strength synthetic sea water as well as in distilled water (Chandralata Raghukunar, Trevor, M. D'Souza, Greg Thorn, and C. A. Reddy. 1999. Lignin-modifying enzymes of *Flavodon flavus* isolated from a coastal marine environment. Applied and Environmental Microbiology, 65: 2103–2111). This was the first report of production of lignin-degrading enzymes in this fungus and also their production in half-strength artificial seawater.

Normally the wastewater disposal includes physical-chemical treatment, waste-minimisation and biological treatment. Most of the biological approaches considered for restoration of PAH-contaminated sites depend on the activity of bacteria. Whereas low-molecular weight-PAH are usually readily degraded, high-molecular weight PAH of five or more rings resist bacterial degradation. White-rot fungi would be expected to have greater access to poorly available substrate, since they secrete extracellular enzymes involved in the oxidation of complex aromatic compounds like lignin. PAHs are recalcitrant, hydrophobic compounds and sorption to biological solids may be a significant mechanism for removal of PAHs from refinery wastewater.

Various white-rot fungi have been tried for biodegradation of PAHs:

(i) A reference may be made to a publication (Sack, U.,Heinz, T. M., Deck, J., Cemglia, C. E., Martens, R., Zadrazil, F. and Fritsche, W. 1997. Comparison of phenanthrene and pyrene degradation by different wood-decaying fungi. Applied and Environmental microbiology 63: 3919–3925) wherein degradation of phenanthrene and pyrene by different wood-decaying fungi is reported. The fungi used were *Trametes versicolor, Laetiporus sulphureus, Kuehneromyces mutabilis, Flammulina velutipes* and *Agrocybe aegerita*. A concentration of 50 $mgL^{+1}$ phenanthrene was used in low nitrogen liquid medium and 3.7% to 15.5% was mineralised in 63 days.

(ii) A reference may be made to a publication (Cuny, P., Faucet, J., Acquaviva, M., Bertrand, J. C. and Gilewicz M. 1999. Enhanced biodegradation of phenanthrene by a marine bacterium in presence of a synthetic surfactant. Letters in Applied Microbiology, 29:242–245), wherein a marine bacterium *Sphingomonas* sp. is reported to degrade about 85% of 4ppm phenanthrene after 8–9 days in the presence of the surfactant Tween 80. However, no reference is about degradation by heat-killed culture.

(iii) A reference may be made to a publication (Cerniglia, C. E. 1984. Microbial metabolism of polycyclic aromatic hydrocarbons. Advances in Applied Microbiology. 30: 31–71) wherein metabolism of PAHs by bacteria, cyanobacteria, fungi and algae is reviewed. Fungi oxidize PAHs via a cytochrome P-450 monooxygenase to form arene oxides. They form glucurnide and sulfate conjugates of phenolic PAHs and these reactions may be important in the detoxification and elimination of PAHs in the environment.

(iv) A reference may be made to a publication (Sack, U., Hofrichter, M. and Fritsche, W. 1997. Degradation of polycyclic aromatic hydrocarbons by manganese-peroxidase of *Nematoloma forwardii*. FEMS-Microbiology Letters 152: 227–234) wherein mineralization of phenanthrene was brought about by a lignin-degrading enzyme, manganese-peroxidase of the white-rot fungus *Nematoloma frowardii* suggesting an important role for white-rot fungi in PAH oxidation. Manganese peroxidase of 1.96 U ml-1 degraded radiolabeled phenanthrene of 10 mg $L^{-1}$ concentraiton (10 ppm) in a period of 7 days. However, using enzyme on a mass scale is an expensive process.

(v) A reference may be made to a publication (Novotny, C., Erbanova, P., Cajthaml, T., Rothschild, N, Dosoretz, C and Sasek, V. 2000. *Irpex lacteus*, a white rot fungus applicable to water and soil bioremediation. Applied Microbiology and Biotechnology 54: 850–853) wherein, the white-rot fungus *Irpex lacteus* was implied in water and soil bioremediation contaminated with PAHs. Live culture and heat-killed control removed 37 and 38% phenanthrene (initial concentration f 25 ppm) spiked in brown soil during 2 months incubation period.

(vi) A reference may be made to a publication (Stringfellow, W. T. and Alvarez Cohen, L. 1999. Evaluating the relationship between the sorption of PAHs to bacterial biomass and biodegradation. Water Research, 33: 2535–2544) wherein sorption of PAHs to biological solids is suggested to be a significant mechanism for removal of PAHs from refinery wastewater.

Although, the fungus strain used here has the same characteristics as already described in the literature, the novelty lies in its new use in the process of PAH removal under fresh water as well as estuarine conditions by employing live as well as heat-killed fungal biomass.

OBJECTS OF THE INVENTION

The main objective of the present invention is to provide a process for removal of three and four-ringed polycyclic aromatic hydrocarbons from wastewater/other contaminated sites using live or dead fungal biomass of the lignin-degrading white-rot fungus *Flavodon flavus* having accession number NRRL 30302 for use in saline waters which obviates drawbacks as detailed above.

Another objective of the present invention is to provide the use of immobilized fungus or its culture filtrate for removal of three and four-ringed polycyclic aromatic hydrocarbons from wastewater/other contaminated sites.

SUMMARY OF THE INVENTION

Thus, the present invention relates to removal of polycyclic aromatic hydrocarbons phenanthrene and chrysene from wastewater and other contaminated sites using *Flavodon flavus* which has been isolated from decaying seagrass in the lagoon at Kavaratti island of the Lakshadweep Islands and deposited at Agricultural Research Service Culture Collection (NRRL), 1815 North University Street, Peoria, Ill. 61604, USA bearing accession number NRRL 30302 on Mar. 10, 2000 and has also at the National Institute of Oceanography, Dona Paula, Goa 403 004, India and having the isolate number NIOCC 312. The said fungus can be grown in synthetic media prepared with distilled water or half-strength seawater. The said fungus can also be grown in conventional media or in powdered sugarcane bagasse suspended in distilled water or half-strength sea water or in 1% sugarcane molasses dissolved in distilled water to raise large biomass of the fungus for application in field trials for bioremediation of soil or water bodies. The fungus thus grown can be immobilized by conventional methods and used for removal of phenanthrene and chrysene from wastewater and other contaminated sites. Alternatively, heat-killed fungal biomass of the said fungus can also be used for bioremediation of phenanthrene or chrysene-contaminated wastewater or sites.

BRIEF DESCRIPTION OF THE ACCOMPANYING DRAWINGS

In the drawings accompanying these specifications,

FIG. 1 represents percentage removal of phenanthrene at 4 parts per million (ppm) concentration by the live and heat-killed cultures of *Flavodon flavus*, strain having accession No. NRRL 30302. Values obtained in two experiments are plotted.

BRIEF DESCRIPTION OF THE ACCOMPANYING TABLES

Figure 1:
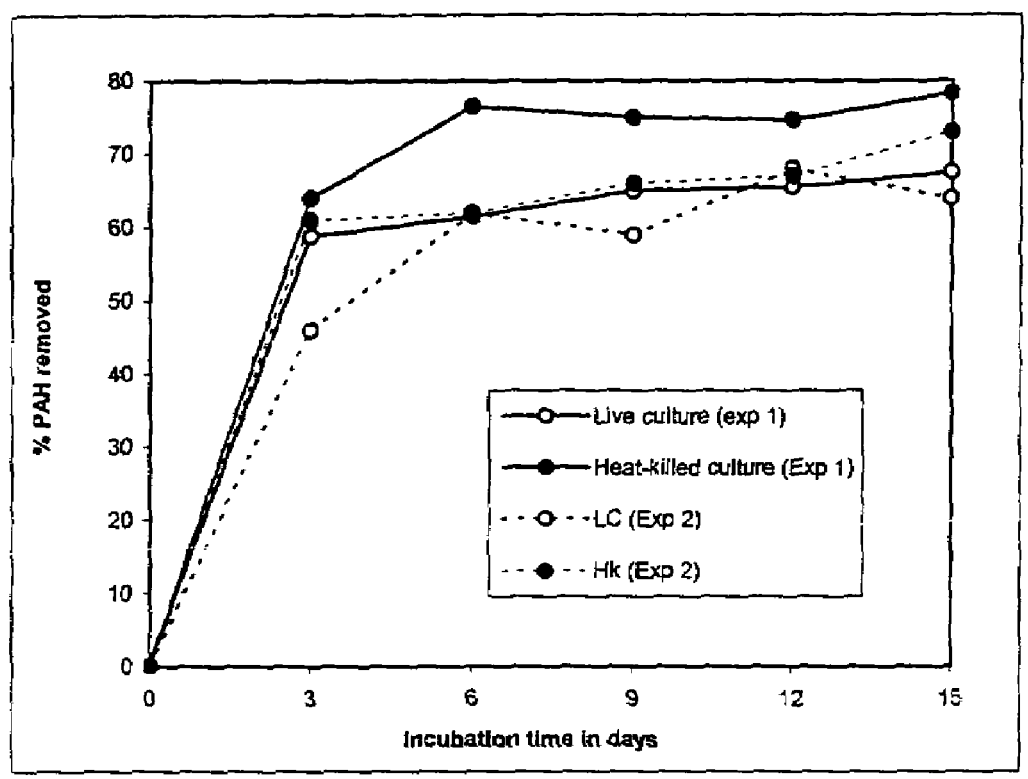

Table 1 represents a comparative statement of phenanthrene degradation by various organisms.

Table 2 represents phenantherene removal by different treatments.

DETAILED DESCRIPTION OF THE PRESENT INVENTION

Accordingly, the present invention provides a process for removal of three-ringed and four-ringed polycyclic aromatic hydrocarbons from waste water and polyaromatic hydrocarbon contaminated sites using white-rot lignin modifying fungus strain *Flavodon flavus* which has been deposited at Agricultural Research Service Culture Collection (NRRL), 1815 North University Street, Peoria, Ill. 61604, USA bearing accession number NRRL 30302 on Mar. 10, 2000 and also at National Institute of Oceanography, Goa 403 004, India, bearing accession No. NIOCC #312, said process comprising: (a) growing the white rot strain *Flavodon flavus* in any conventional nutrient medium containing assimilable carbon and nitrogen source for at least 7 days; (b) contacting the said water/sites contaminated by three-ringed and four-ringed polycyclic aromatic hydrocarbons with 7-day old heat-killed or live fungal bio-mass of *Flavodon flavus* under oxygenated conditions with salinity ranging between 0 to 15 parts per thousand, for a minimum period of 3 to 6 days and, (c) removing said heat-killed or live fungal bio-mass by any conventional method to get the water/site devoid of polycyclic aromatic hydrocarbons.

In an embodiment of the present invention, the three-ringed polycyclic aromatic hydrocarbon is phenanthrene.

In another embodiment of the present invention, the four-ringed polycyclic aromatic hydrocarbon is chrysene.

In still another embodiment of the present invention, the carbon source for growing the fungus used is glucose at 10% concentration.

In yet another embodiment of the present invention, the nitrogen source used for growing the fungus is low nitrogen source.

In a further embodiment of the present invention, the nitrogen source is ammonium tartrate.

In one more embodiment of the present invention, the age of the said fungal culture is at least 7 days to get maximum removal of phenanthrene or chrysene.

In one another embodiment of the present invention, said fungus can be used as live or heat-killed culture.

In an embodiment of the present invention, the removal of phenanthrene or chrysene can be done in the presence of seawater.

In another embodiment of the present invention, the pre-grown fungal culture should be in contact with phenanthrene or chrysene for a minimum of 7 days for effective removal.

In still another embodiment of the present invention, live or heat-killed *Flavodon flavus* fungus can be immobilized in polyurathene foam cubes and used for removal of phenanthrene or chrysene from any medium.

In yet another embodiment of the present invention, culture filtrate from the live culture of the said fungus can be used for removal of phenanthrene or chrysene.

The organism given in the present invention is a white-rot basidiomycete fungus isolated from decaying marine plant from a coastal marine environment and identified as *Flavodon flavus*. The said fungus *F. flavus* can be grown in malt extract broth containing 2% malt extract and 0.3% peptone in distilled water. The fungal mat grown this way may be macerated and used as starter inoculum for the experimental cultures of synthetic media prepared in distilled water or in half-strength seawater. The synthetic media can be prepared in distilled water or half-strength seawater containing 10% glucose as carbon source, 2.4 mM ammonium tartrate as the nitrogen source, thiamine, trace metal solution, macro element solution containing potassium and magnesium salts, Tween 80, veratryl alcohol and 20 mM sodium acetate buffer at pH 4.5. This medium is referred to as low nitrogen medium. An example for the process for removal of PAH involves addition of filter-sterilized phenantherene at 4 ppm concentration, to 7 day old cultures *F. flavus* growing in various media as described above. The removal of phenantherene is monitored spectroflorometrically by extracting the residual phenanthrene in hexane saturated with sodium sulfite (for removal of moisture) measuring absorbance at excitation and emission wave lengths of 310 and 360 nm respectively (Keizer, P. D. and Gordon, D. C. Jr. 1973. Detection of trace amounts of oil in sea water by fluorescence spectroscopy. J. Fish. Res. Bd. Can. 30: 1039–1046) every third day up to 15 days. Heat-killed cultures serve as controls where sufficient removal takes place due to adsorption.

The said fungus *Flavodon flavus*, deposited at Agricultural Research Service Culture Collection (NRRL), 1815 North University Street, Peoria, Ill. 61604, USA bearing accession number NRRL 30302 on Mar. 10, 2000, is capable of growing in the presence of salts whose concentration is similar to that found in half-strength sea water. Most of the industrial effluents contain high concentrations of salts, especially chlorides and sulfates (Bartlett, R. E. 1971. Public health Engineering design in Metric Wastewater Treatment, Applied Science Publishers, London). In light of this, salt tolerant organisms are better suited for such wastewater treatments. Most of the fungi used for bioremediation of such wastewater have not been tested for their salt tolerance. In view of this, the present process has an advantage over the conventional processes referred to in various patents discussed above. A comparative statement of the degradation of phenanthrene given in the prior art and that of the present invention is made in Table 1.

TABLE 1

A comparative statement of phenanthrene degradation by various organisms

| Reference | Organism | Concentration of phenanthrene | Extent of degradation | Time |
| --- | --- | --- | --- | --- |
| Sack et al. 1997 | 5 wood-decaying fungi | 50 ppm | 3.7–15.5% | 63 days |
| Cuny et al. 1999 | A marine strain of the bacterium *Sphingomonas* sp | | 85% | 8 days |

TABLE 1-continued

A comparative statement of phenanthrene degradation by various organisms

| Reference | Organism | Concentration of phenanthrene | Extent of degradation | Time |
| --- | --- | --- | --- | --- |
| Sack et al. 1997 | Manganese peroxidase enzyme of the fungus Nematoloma frowardii | 10 ppm | 2.5% | 7 days |
| Novotny et al. 2000 | Irpex lacteus | 25 ppm mixed with brown soil | 37% by live and 38% by heat-killed culture in soil. | 60 days |
|  |  | Liquid culture | No removal observed. | up to 14 days |
| Stringfellow and Cohen 1999 | Bacterial biofilm for biosorption and biodegradation | 0.5 to 5.0 µM | Removed by biosorption | Not mentioned |
| Present invention | Flavodon flavus, live and heat-killed culture | 4 ppm | 70–80% | 6–7 days |

The following examples are given by way of illustrations of the present invention and therefore should not be construed to limit the scope of the present invention.

EXAMPLE 1

The ability of Flavodon flavus, deposited at Agricultural Research Service Culture Collection (NRRL), 1815 North University Street, Peoria, Ill. 61604, USA bearing accession number NRRL 30302 on Mar. 10, 2000, to remove a three-ringed and four-ringed PAHs, phenanthrene and chrysene respectively from a low nitrogen medium (LNM) containing high carbon source was carried out as follows: The low nitrogen mediaum can be prepared in distilled water or half-strength seawater containing 10% glucose as carbon source, 2.4 mM ammonium tartrate as the nitrogen source, thiamine, trace metal solution, macro element solution containing potassium and magnesium salts, Tween 80, veratryl alcohol and 20 mM sodium acetate buffer at pH 4.5. The culture of F. flavus was raised in LNM using agar plugs from the Petri plate containing the fungus growing on malt extract agar medium. A ten-day old culture in LNM was macerated by adding sterilised glass beads or in a blender to prepare the inoculum. To 9 ml of LNM, 1 ml of such macerated fungal mycelium was added. The flasks were oxygenated immediately after inoculation and every alternate day thereafter. After 7 days, one set of flasks were heat-killed by autoclaving for 20 min. 20 µl of 4 ppm phenanthrene dissolved in hexane and filter-sterilized, were added to these cultures and the flasks were oxygenated. Two flasks of live and two of heat-killed cultures were filtered at regular intervals. The culture supernatants were extracted with distilled hexane and the concentration of residual phenanthrene was determined by fluorescence spectroscopy at excitation and emission wavelengths of 310 and 360 nm respectively using a spectrofluorometer of (Keizer, P. D. and Gorgon, D. C. Jr. 1973. Detection of trace amounts of oil in seawater by fluorescence spectroscopy. J. Fish. Res. Bd. Can 30: 1039–1046). The results are calculated as the difference in percentage between initial 0-day readings and the day of further measurements of residual phenanthrene. The percentage removal is further calculated from these results.

Accordingly, FIG. 1 shows the results of two experiments where about 40–50% of phenanthrene was removed on the third day by live as well as heat-killed culture and by 15 days about 70–80% is removed.

EXAMPLE 2

The ability of Flavodon flavais, deposited at Agricultural Research Service Culture Collection (NRRL), 1815 North University Street, Peoria, Ill. 61604, USA bearing accession number NRRL 30302 on Mar. 10, 2000, to remove phenanthrene with cultures started with different inoculum concentration was tested with live and heat-killed cultures as follows: To 9 ml of LNM, inoculum containing 0.25, 0.5, 0.75, 1.00, 1.25 and 1.5 mg of fungal dry weight was added and the cultures were grown for 7 days. After adding 4 ppm phenanthrene the cultures were filtered on day 7 and the residual phenanthrene was extracted with hexane and measured as explained in the Example 1.

Figure 2:
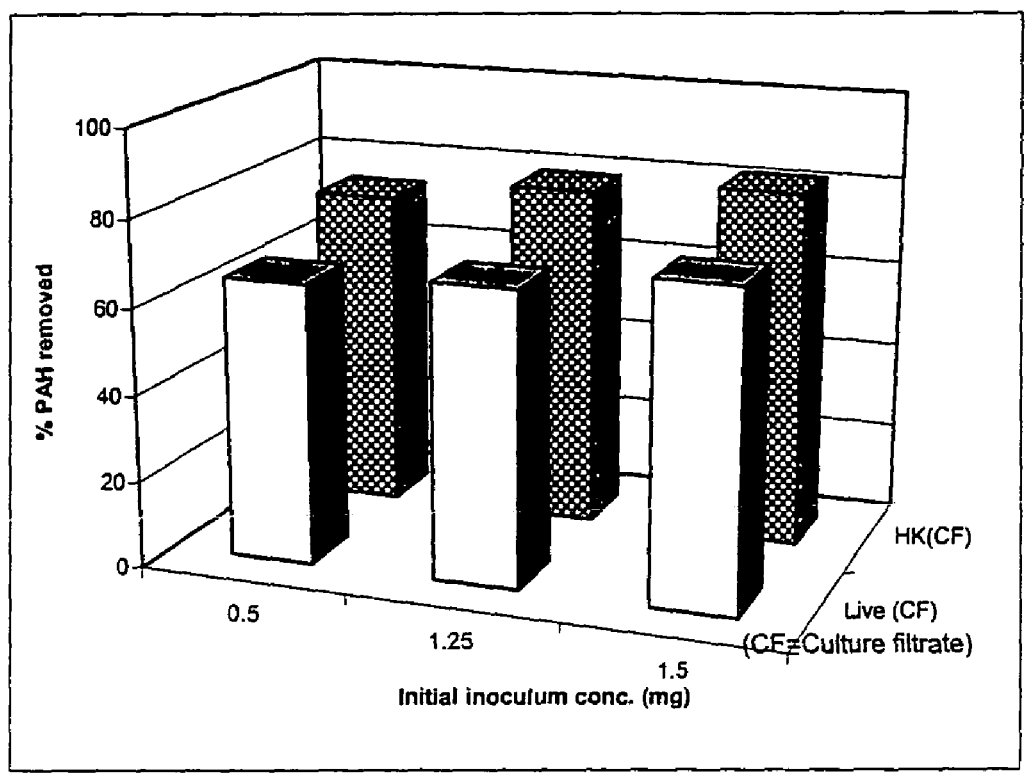
FIG. 2 represents percentage phenanthrene removed by live and heat-killed fungal biomass at the end of 6 days by cultures started with varying inoculum concentrations.
Figure 3:
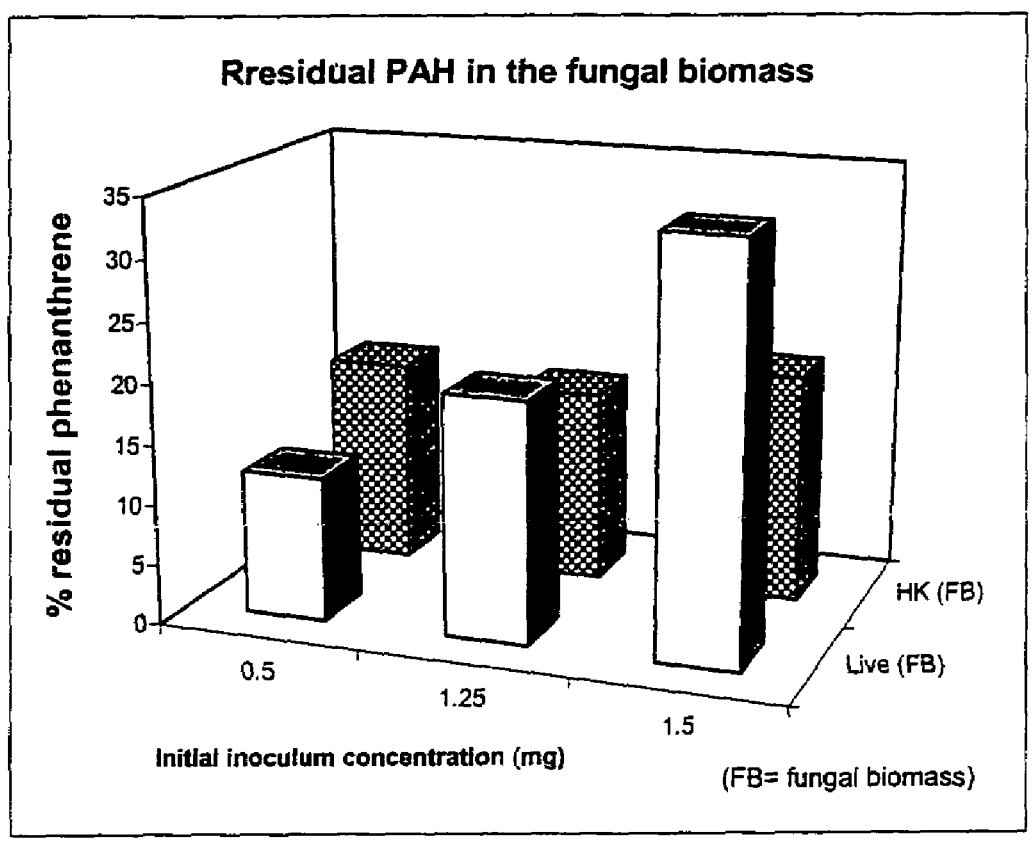
FIG. 3 represents residual phenanthrene in the live and heat-killed fungal biomass of the culture initiated with different inoculum concentrations.

Accordingly, FIG. 2 shows almost similar percentage of phenanthrene removed by live and heat-killed culture with different fungal inoculum concentrations. FIG. 3 shows the residual phenanthrene extracted from the fungal bio-mass of live and heat-killed cultures, where the amount remaining on live cultures is more than in heat-killed cultures.

EXAMPLE 3

Effect of phenanthrene on the growth of Flavodon flavus was studied as follows; To 9 ml LNM 1 ml of macerated fungal inoculum was added, with one set of flasks receiving 4 ppm concentration of phenanthrene dissolved in 20 µl hexane and control flasks receiving only hexane. Three flasks from each treatment were filtered over pre-weighed GF/C filters and the fungal bio-mass was dried to a constant weight at 60° C. The difference in weight was calculated as fungal dry weight in mg.

Figure 4:
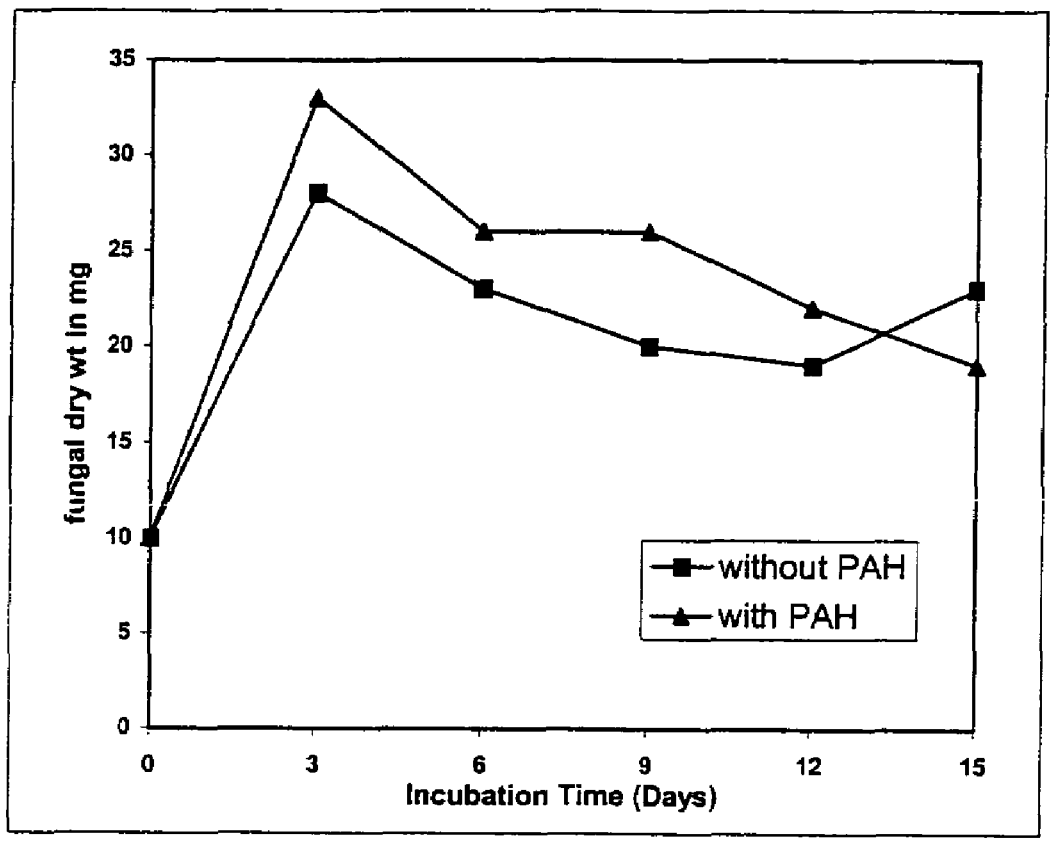
FIG. 4 represents effect of phenanthrene at 4 ppm concentration on the growth of *Flavodon flavus*.

Accordingly, FIG. 4 shows that growth was slightly better in the presence of phenanthrene.

EXAMPLE 4

The ability of *Flavodon flavus* to degrade phenanthrene in seawater medium was tested as follows: The culture was grown in LNM prepared with half-strength seawater and the other procedures were same as those described in Example 1.

Figure 5:
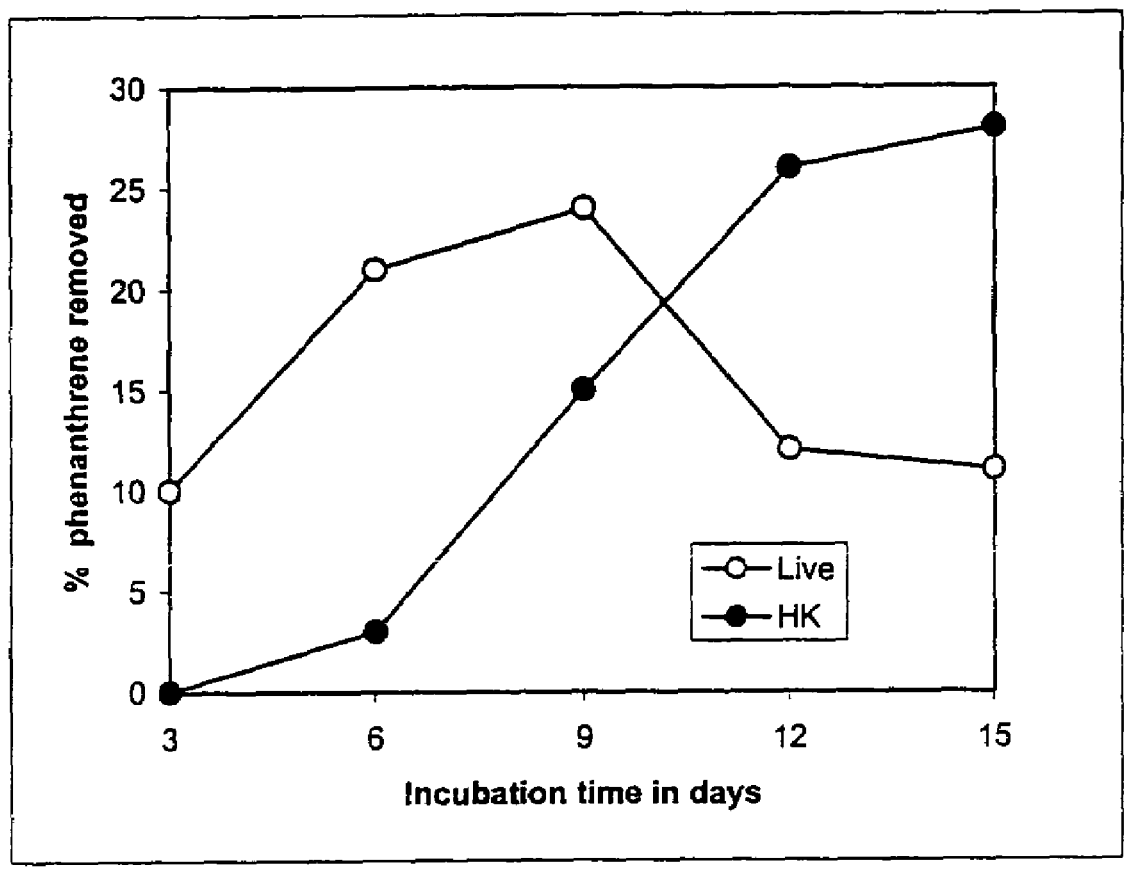
FIG. 5 represents removal of phenanthrene at 4 ppm concentration by live and heat-killed cultures of *F. flavus* grown in half-strength seawater medium.

Accordingly, FIG. 5 shows that live and heat-killed cultures of *F. flavus* removed about 20–30% of phenanthrene within 7 days.

EXAMPLE 5

The ability of *Flavodon flavus* to degrade four-ringed PAH, chrysene was similarly tested in LNM.

Figure 6:
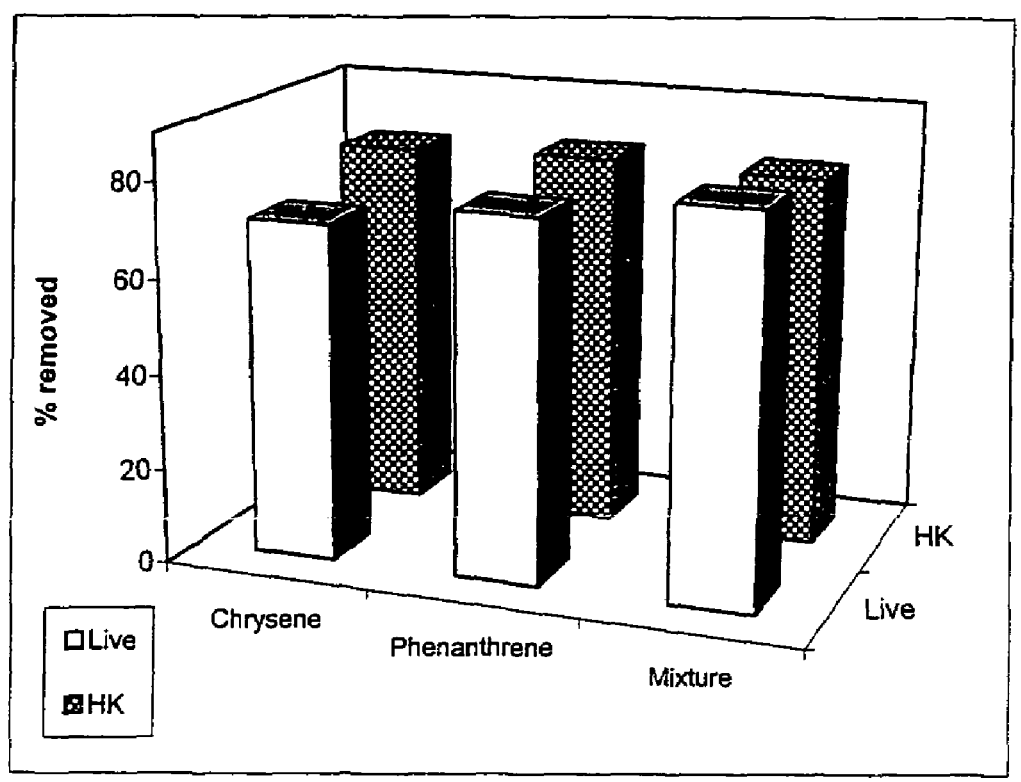
FIG. 6 represent removal of phenanthrene, chrysene and a mixture of the two by live and heat-killed culture of *F. flavus*.

Accordingly, FIG. 6 shows degradation of chrysene (4 ppm concentration) in comparison with phenanthrene and a mixture of the two by live and heat-killed cultures after 6 days.

EXAMPLE 6

*Flavodon flavus* was immobilised in foam cubes and these were used for removal of phenanthrene from LNM. Accordingly, Table 1 show that live and heat-killed cultures were capable of removing phenanthrene. Culture supernatant from live culture when incubated with phenanthrene also removed about 43% of phenanthrene within 3 days.

TABLE 2

Phenanthrene removal by different treatments.

| Treatment | % Phenanthrene removed | |
|---|---|---|
| | Live culture | Heat-killed culture |
| Immobilized fungus | 56 | 28 |
| Culture supernatant | 43 | Not defined |

The Main Advantages of the Present Invention are:
1. The fungus *Flavodon flavus* removes about 70–80% phenanthrene within 5–7 days.
2. Heat-killed culture of *Flavodon flavus* also removes about 70–80% phenanthrene within 5–7 days. None to very little residual phenanthrene is detected in the fungal bio-mass at the end of 6$^{th}$ day incubation period.
3. The fungus removes 20–30% phenanthrene when grown in half-strength sea water also and thus can be used in effluents containing salts or in estuarine conditions where the salinity ranges from 0 to 15 parts per thousand.
4. Immobilised fungus or culture supernatant also is capable of removing phenanthrene within 3–7 days.

We claim:

1. A process for removal of three-ringed and/or four-ringed polycyclic aromatic hydrocarbons from sites contaminated therewith using white-rot lignin modifying fungus strain *Flavodon flavus* NRRL 30302, said process comprising:
    (a) growing the white rot strain *Flavodon flavus* NRRL 30302 in a nutrient medium containing assimilable carbon and nitrogen source for at least 7 days;
    (b) contacting, for at least 3 days, the sites contaminated by the three-ringed and/or four-ringed polycyclic aromatic hydrocarbons with a fungal bio-mass of the *Flavodon flavus* grown in step (a) under oxygenated conditions with salinity ranging between 0 to 15 parts per thousand, and
    (c) removing said fungal bio-mass to get the contaminated sites devoid of three-ringed and/or four-ringed polycyclic aromatic hydrocarbons.

2. The process as claimed in claim 1, wherein the three-ringed polycyclic aromatic hydrocarbon is phenanthrene.

3. The process as claimed in claim 1, wherein the four-ringed polycyclic aromatic hydrocarbon is chrysene.

4. The process as claimed in claim 1, wherein the carbon source for growing the fungus used is glucose at 10% concentration.

5. The process as claimed in claim 1, wherein the nitrogen source is ammonium tartrate.

6. The process as claimed in claim 1, wherein the fungal biomass used in step (b) is a live culture.

7. The process as claimed in claim 1, wherein the removal of the three-ringed polycyclic aromatic hydrocarbon and/or the four-ringed polycyclic aromatic hydrocarbon is conducted in the presence of seawater.

8. The process as claimed in claim 1, wherein the fungal biomass of *Flavodon flavus* grown in step (a) is contacted with the three-ringed polycyclic aromatic hydrocarbon and/or the four-ringed polycyclic aromatic hydrocarbon for a minimum of 7 days.

9. The process as claimed in claim 1, wherein the fungal biomass of *Flavodon flavus* used in step (b) is live or heat killed and is immobilized in polyurethane foam cubes.

10. A process for removal of three-ringed and/or four-ringed polycyclic aromatic hydrocarbons from sites contaminated therewith using white-rot lignin modifying fungus strain *Flavodon flavus* NRRL 30302, said process comprising:
    (a) growing the white rot strain *Flavodon flavus* NRRL 30302 in a nutrient medium containing assimilable carbon and nitrogen source for at least 7 days;
    (b) contacting, for at least 3 days, the sites contaminated by the three-ringed and/or four-ringed polycyclic aromatic hydrocarbons with culture filtrate from the *Flavodon flavus* grown in step (a) under oxygenated conditions with salinity ranging between 0 to 15 parts per thousand, and
    (c) removing said culture filtrate to get the contaminated sites devoid of three-ringed and/or four-ringed polycyclic aromatic hydrocarbons.

11. The process as claimed in claim 1, wherein the contaminated sites include waste water contaminated with the three-ringed and/or four-ringed polycyclic aromatic hydrocarbons.

12. The process as claimed in claim 1, wherein, in step (a), the *Flavodon flavus* is grown for 7 days.

13. The process as claimed in claim 1, wherein the fungal bio-mass of *Flavodon flavus* used in step (b) is a heat-killed culture.

14. The process as claimed in claim 7, wherein the three-ringed polycyclic aromatic hydrocarbon is phenanthrene and the four-ringed polycyclic aromatic hydrocarbon is chrysene.

15. The process as claimed in claim 8, wherein the three-ringed polycyclic aromatic hydrocarbon is phenanthrene and the four-ringed polycyclic aromatic hydrocarbon is chrysene.

16. The process as claimed in claim 9, wherein the three-ringed polycyclic aromatic hydrocarbon is phenanthrene and the four-ringed polycyclic aromatic hydrocarbon is chrysene.

17. The process as claimed in claim 10, wherein the three-ringed polycyclic aromatic hydrocarbon is phenanthrene and the four-ringed polycyclic aromatic hydrocarbon is chrysene.

* * * * *